(12) United States Patent
Han et al.

(10) Patent No.: US 11,371,036 B2
(45) Date of Patent: Jun. 28, 2022

(54) ORALLY ADMINISTERED COMPOSITION OF METHIONINASE ENZYME

(71) Applicants: Qinghong Han, San Diego, CA (US); Robert M Hoffman, San Diego, CA (US)

(72) Inventors: Qinghong Han, San Diego, CA (US); Robert M Hoffman, San Diego, CA (US)

(*) Notice: Subject to any disclaimer, the term of this patent is extended or adjusted under 35 U.S.C. 154(b) by 0 days.

(21) Appl. No.: 17/225,677

(22) Filed: Apr. 8, 2021

(65) Prior Publication Data

US 2021/0254040 A1 Aug. 19, 2021

Related U.S. Application Data

(63) Continuation of application No. 16/165,879, filed on Oct. 19, 2018, now Pat. No. 11,001,826.

(51) Int. Cl.
| | |
|---|---|
| *A61K 38/51* | (2006.01) |
| *C12N 9/88* | (2006.01) |
| *A61K 31/675* | (2006.01) |
| *A61K 47/02* | (2006.01) |
| *A61P 35/00* | (2006.01) |
| *A61P 3/10* | (2006.01) |
| *A61K 9/00* | (2006.01) |

(52) U.S. Cl.
CPC .............. *C12N 9/88* (2013.01); *A61K 9/0053* (2013.01); *A61K 31/675* (2013.01); *A61K 38/51* (2013.01); *A61K 47/02* (2013.01); *A61P 3/10* (2018.01); *A61P 35/00* (2018.01); *A61K 9/0095* (2013.01); *C12Y 404/01011* (2013.01)

(58) Field of Classification Search
None
See application file for complete search history.

(56) References Cited

U.S. PATENT DOCUMENTS

| | | | |
|---|---|---|---|
| 11,001,826 B2* | 5/2021 | Han | C12N 9/88 |
| 2005/0031606 A1* | 2/2005 | Tan | A61K 31/135 |
| | | | 424/94.4 |
| 2014/0205583 A1* | 7/2014 | Yagi | A61K 31/675 |
| | | | 424/94.3 |

OTHER PUBLICATIONS

Yoshioka T. et al. Anticancer Efficacy In Vivo and In Vitro, Synergy with 5-Fluorouracil, and Safety of Recombinant Methioninase. Cancer Research 58(12)2583-2587 1998. (Year: 1998).*
Yang, Z. et al. Pharmacokinetics, Methionine Depletion, and Antigenicity of Recombinant Methioninase in Primates. Clinical Cancer Research 10(6)2131-2138 2004. (Year: 2004).*
Sun, X. et al. In Vivo Efficacy of Recombinant Methioninase Is Enhanced by the Combination of Polyethylene Glycol Conjugation and Pyridoxal 5' Phosphate Supplementation. Cancer Research 63:8377-83, Dec. 2003. (Year: 2003).*

* cited by examiner

*Primary Examiner* — Ralph J Gitomer
(74) *Attorney, Agent, or Firm* — Barry Choobin; Patent 360

(57) ABSTRACT

A composition and method for lowing serum and plasma levels of methionine by oral administration. The composition includes a recombinant methioninase enzyme and a cofactor (pyridoxal-L-phosphate). Methods of use describe methods for treatment of cancer, including malignant melanoma, by oral administration of the methioninase composition. Methods for chronic suppressive therapy of melanoma and other cancers are described. Because reduction of plasma methionine levels is effective in treating other conditions, including diabetes and conditions associated with aging, the use of the methods described herein includes treatment of these and other conditions.

3 Claims, 1 Drawing Sheet

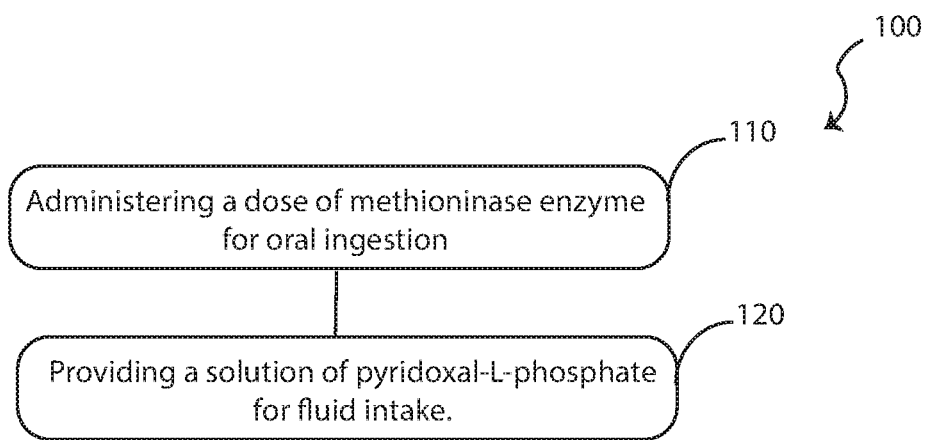

ORALLY ADMINISTERED COMPOSITION OF METHIONINASE ENZYME

CROSS REFERENCE TO RELATED APPLICATION

This application is a continuation of a U.S. Non-Provisional application Ser. No. 16/165,879 filed Oct. 10, 2018, which claims priority from a U.S. Provisional Patent Application Ser. No. 62/574,693 filed Oct. 19, 2017, the entire contents of both the applications are incorporated herein by reference.

FIELD OF INVENTION

This invention relates to compositions and methods for lowering serum methionine levels. In particular, the invention involves an orally administered composition including a methionine-ase enzyme and methods of use.

BACKGROUND

Metastatic melanoma is a recalcitrant cancer, with a five-year survival rate of only 7%-30%. There is currently no cure for stage III and stage IV disease.

An excessive requirement for methionine appears to be a metabolic defect in cancer, and the only known such metabolic defect shared by cells across most types of cancer cells. This elevated methionine ("MET") use by cancer cells is termed "methionine dependence ("MET dependence"). It has been previously shown that growth of cancer cells can be selectively arrested by methionine deprivation, such as with recombinant methioninase ("rMETase").

Restriction of dietary MEI reduces serum MET levels and is known to reverse age-related changes and increase lifespan in some animals, decrease the severity of or eliminate insulin-resistant diabetes mellitus, and impair or reverse the grown of certain malignancies. Severe dietary MET restriction is necessary to achieve observable effects and, generally, requires elimination of essentially all animal protein and many plant-based foods from the diet.

Means other than dietary restriction have been used to decrease serum MET. Targeting MET by administration of recombinant methioninase ("rMETase") can arrest the growth of cancer cells in vitro and in vivo, presumably by decreasing MEI concentration in the tumor interstitial microenvironment. Because METase was thought to be hydrolyzed at an acid pH in the stomach and then further degraded by enterokinase-activated proteolytic enzymes in the small bowel, exploitation of METase to lower serum concentrations of methionine without dietary methionine restriction has required METase to be administered parenterally.

Ideally, a composition containing rMETase with is effective following oral administration is needed to exploit METase to lower serum MET levels without the need for severe dietary restriction or parental dosing.

SUMMARY OF THE INVENTION

Embodiments of the present invention include a METase-containing composition effective in reducing serum MET levels and methods of use to treat cancer, insulin-resistant diabetes mellites, and to reverse age-related metabolic and tissue degenerative changes in animals and humans.

Disclosed is a composition for oral administration to reduce serum methionine levels in an individual comprising a methioninase enzyme; a cofactor; and a phosphate-buffered saline solution.

In some embodiments, the methioninase enzyme is a L-methionine α-deamino-γ-mercaptomethane lyase in some embodiments, the cofactor is pyridoxal-L-phosphate. In some embodiments, the pyridoxal-L-phosphate is in an aqueous solution at a concentration of about twenty (20) millimoles per liter of water.

Disclosed is a method for suppressing the growth of a malignancy within an individual comprising the steps of administering an oral dose of methioninase enzyme; and providing a solution of pyridoxal-L-phosphate for fluid intake.

In some embodiments, the dose of methioninase enzyme is about one hundred (100) mg/kg of body weight.

In some embodiments, the malignancy is melanoma. In some embodiments, the malignancy is Ewing's sarcoma.

In some embodiments, the individual is a human individual. In some embodiments, the individual is a non-human individual. In some embodiments, the non-human individual is a mouse.

Disclosed is a method for preventing a disease condition in an individual comprising the steps of administering an oral dose of methioninase enzyme; and providing a solution of pyridoxal-L-phosphate for fluid intake.

In some embodiments, the disease condition is cancer. In some embodiments, the disease condition is insulin resistant diabetes mellitus. In some embodiments, the disease condition is condition related to aging.

In some embodiments, the individual is a human individual. In some embodiments, the individual is a non-human individual.

The foregoing and other features and advantages of the present invention will be apparent from the following more detailed description of the particular embodiments of the invention, as illustrated in the accompanying drawings.

BRIEF DESCRIPTION OF THE DRAWING

FIG. 1 is a flow chart of a method of oral administration of a METase composition to treat a disease condition.

DETAILED DESCRIPTION

There are multiple instances wherein rMETase has been shown effective to suppress the growth of tumor cells. As previously mentioned, targeting MET by recombinant methioninase ("rMETase") can arrest the growth of cancer cells in vitro and in vivo. Administration of rMETase by intra-peritoneal injection ("ip-rMETase") inhibits tumor growth in a patient-derived orthotopic xenograft ("PDOX") model of a BRAF-V600E mutant melanoma. When the efficacy of rMETase in combination with a first-line melanoma drug, temozolomide (TEM), combination therapy of TEM, first line therapy, and rMETase is significantly more efficacious than any of these monotherapies. Additionally, rMETase if efficacious against Ewing's sarcoma in a PDOX model, wherein rMETase effectively reduced tumor growth compared to untreated control mice. Serum and tumor MET levels were lower in the rMETase group, versus controls.

MET dependence is a general metabolic defect in cancer. Deprivation of MET arrests growth and induces a tumor-selective G2-phase cell cycle arrest of cancer cells in vitro and in vivo.

MET dependence is believed to be due to excess use of MET for aberrant transmethylation reactions in the cancer cell, termed the "Hoffman effect," analogous to the Warburg effect for elevated glucose use in cancer. For example, the excessive and aberrant use of MET by cancer cells is strongly observed using in positron emission tomography ("PET") scanning following administration of a ['11C]MET-labeled substrate, where uptake of [11C]MET results in a very strong and selective tumor signal compared with normal tissue background. Additionally, [11C]MET is superior to [18C] fluorodeoxyglucose ("FEG")-PET for PET imaging, suggesting MET dependence is more tumor-specific than glucose dependence.

In humans, MET is sourced mainly from food and restriction of dietary MET intake results in lower serum MET levels. MET restriction through diet with low protein content is problematic, however, because the severe restriction of dietary protein necessary to lower serum MET levels does not allow the maintenance of good nutritional status. Use of dietary MET restriction to lower MET levels is also limited by metabolic pathways to also source MET by breaking down protein in tissues. Conversely, the use of parenteral rMETase leads to further reduction of plasma MET and is accompanied by reduction in tumor size.

When compared with ip-rMETase, oral rMETase ("o-rMETase") is significantly more effective as an anticancer agent than ip-rMETase, provided administration of the o-rMETase is accompanied by pyridoxal-L-phosphate ("PLP") in drinking water.

An oral composition of recombinant METase that can be used for cancer treatment, cancer prevention, and anti-aging, ingested on a chronic basis along with PLP is disclosed. Various concentrations of o-rMETase are used, in some embodiments, for the purposes mentioned above.

In a non-limiting experimental example, melanoma PDOX nude mice were randomized into four (4) groups of five (5) mice each: 1) untreated control; 2) ip-rMETase (100 units, intra-peritoneal for fourteen (14) consecutive days; 3) o-rMETase (100 units/2.0 mg. in phosphate-buffered saline ("PBS"); and 4) o-rMETase and ip-rMETase (100 units oral rMETase plus 100 units intraperitoneal rMETase.) Additionally, drinking water containing 100 μmol/L of PLP (1.0 ml of 20 mmol/L PLP solution added to 200 ml drinking water, mixed fresh daily) was provided to all mice for the fourteen (14) day duration of the study. The o-rMETase (100 units/2.0 mg in PBS) was administered daily by gavage using a stainless feeding needle.

All treatments inhibited tumor growth on day fourteen (14) after treatment initiation, compared to untreated control mice (ip-rMETase, $p<0.0001$; o-rMETase, $p<0.0001$; o-rMETase+rMETase, $p<0.0001$). The o-rMETase treatment was significantly more effective than ip-rMETase ($p=0.0086$). The o-rMETase ip-rMETase was significantly more effective than either monotherapy ($p=0.0005$; o-rMETase, $p=0.0367$).

Post-treatment plasma MET levels significantly decreased compared to untreated controls (ip-rMETase, $p=0.122$; o-rMETase, $p=0.003$; o-rMETase ip-rMETase, $p<0.0001$ (FIG. 3). Body weight loss was not observed in any treatment groups (FIG. 4). There were no animal deaths an any group. These results show the safety of o-rMETase and its potential for chronic cancer treatment in a clinical setting.

Mice

Athymic nu/nu nude mice (AntiCancer Inc., San Diego, Calif.), four (4) to six (6) weeks old were used in this study. Mice were housed in a barrier facility in a high-efficacy particulate arrestance ("HEPA")-filtered rack under standard conditions of 12-hour light/dark cycles. The animals were fed an autoclaved laboratory rodent diet. All animal studies were conducted in accordance with the principles and procedures outlined in the National Institutes of Health Guide for the Care and Use of Animals under Assurance Number A3873-1. All mouse surgical procedures and imaging were performed with the animals anesthetized by subcutaneous injection of a ketamine mixture comprising 0.02 ml solution of ketamine at a dose of 20 mg/kg, 15.2 mg/kg xylazine, and 0.48 mg/kg acepromazine maleate. The response of animals during surgery was monitored to ensure adequate depth of anesthesia. The animals were observed daily and humanely sacrificed by CO2 inhalation if they met the following humane endpoint criteria: severe tumor burden, defined as any tumor greater than 20 mm in diameter; prostration; significant body weight loss; difficulty breathing; rotational motion; and drop in body temperature.

Patient-Derived Tumor

A 75 year-old female patient was previously diagnosed with a BRAF-V600E melanoma of the right chest wall. The tumor was previously resected in the Department of Surgery, University of California, Los Angeles ("USLA"). Written informed consent was provided by the patient, and the Institutional Review Board ("IRB") of UCLA approved this experiment.

Establishment of PDOX Models of Melanoma by Surgical Orthotopic Implantation (SOI)

Subcutaneously-grown BRAF V600 mutant melanoma was harvested and cut into small fragments measuring about 3 mm2. After nude mice were anesthetized with the ketamine solution described herein above, a skin incision was made on the right chest into the chest wall, which was split to make space for the melanoma tissue fragment. A single tumor fragment was implanted orthotopically into the space to establish the PCOX model. The wound was closed with 6-0 nylon suture (Ethicon, Inc., NJ, USA), Recombinant Methioninase (rMETase) Production Recombinant L-methionine α-deamino-γ-mercaptomethane lyase (methioninase, METase) [EC 4.4.1.11] from *Pseudomonas putida* has been previously cloned and was produced in *Escherichia coli* (AntiCancer, Inc., San Diego, Calif.). The rMETase is a homotetrameric PLP enzyme of 172-kDa molecular mass.

Formulation of o-rMETase and Pyridoxal-L-Phosphate (PLP) Supplement

Mouse drinking water contained 100 μmol/L PLP. One (1.0) ml of 20 nmol/L PLP was added to 200 ml drinking water and made fresh daily. Approximately two (2) mg (100 units) rMETase in PBS was administered daily by gavage using a stainless feeding needle.

Treatment Study Design in the PDOX Model of Melanoma

BRAF V600E mutant melanoma PDOX nude mice were randomized into four (4) groups of five (5) mice each. The four groups included an: 1) untreated control; 2) ip-rMETase (100 units, intra-peritoneal); 3) o-rMETase (100 units/2.0 mg. orally in PBS and 4) combination of o-rMETase and ip-rMETase (100 units oral rMETase plus 100 units intraperitoneal rMETase). Each group was treated for fourteen (14) consecutive days.

Determination of Plasma Methionine

The plasma methionine concentration was measured using a precolumn derivatization, followed by high-performance liquid chromatography separation based on a previously described method with modification. A 10-μl plasma sample or methionine standard was used. The plasma methionine was identified by the retention time of a methionine standard curve. The limit of detection was 0.5 μM methionine. The upper limit of detection for methionine for methionine assay is about 100 µM.

Statistical Analysis

JMP version 11.0 was used for all statistical analysis. Significant differences for continuous variables were determined using the Mann-Whitney U test. Line graphs expressed average values and error bar showed standard deviation. A probability value of less than or equal to 0.05 was considered statistically significant.

Orally administered rMETase is significantly more effective at inhibiting melanoma tumor growth than intraperitoneal rMETase. There is potential for clinical development of treatment methods exploiting compositions containing o-rMETase administered with PLP as an agent for chronic cancer therapy and prevention, and, possibly, for life extension because dietary MET reduction extends lifespan in many animal models.

FIG. 1 is a flow chart of a method of oral administration of a METase composition to treat a disease condition. FIG. 1 shows a method 100 comprising an administering step 110 and a providing step 120.

Administering step 110, in some embodiments, comprises administering an oral dose of methioninase enzyme. Wherein the disease condition is a disease condition in a human individual, administering step 110 comprises giving the individual an oral formulation of the methioninase enzyme, which, in some embodiments, includes one or more excipients, such as flavors, sweeteners, binders, other excipients used in oral dosing of medications and other compositions for human individuals. This is not meant to be limiting; in some embodiments, method 100 is undertaken with a non-human individual, such as a pet animal, a livestock animal, or a laboratory animal such as a mouse.

Providing step 120, in some embodiments, comprises providing a solution of pyridoxal-L-phosphate for fluid intake. The solution may additionally comprise a flavor, a sweetener, a thickener, and the like, in some embodiments.

Variations of method 100 are used, in some embodiments, to suppressing the growth of a malignancy, including, but not limited to, malignant melanoma and Ewing's sarcoma. Because the tumor suppressive effects of lowering the plasma concentration of methionine in the tumor microenvironment are known for many malignancies, this disclosure anticipates the use of method 100 to treat many other malignancies. It is additionally within the scope of this disclosure for method 100 to be used as chronic suppressive therapy for melanoma, Ewing's sarcoma, and many other malignancies. Moreover, it is within the scope of this disclosure to employ step 110 and step 120 of method 100 to treat insulin-resistant diabetes, and in the treatment various neurodegenerative, musculoskeletal degenerative, inflammatory, and immunodeficiencies associated with normal aging process, and to reverse many effects of normal aging. It is additionally within the scope of method 100 to treat other diseases or conditions wherein reduction of plasma methionine levels is beneficial in the treatment, suppression, or prevention of the condition.

The embodiments and examples set forth herein were presented to best explain the present invention and its practical application, and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above and are intended to fall within the scope of the appended claims.

What is claimed is:

1. A composition for oral administration to reduce serum methionine levels in an individual in need thereof comprising:
   a methioninase enzyme;
   pyridoxal-L-phosphate as a cofactor; and
   a phosphate-buffered saline solution.

2. The composition of claim 1, wherein the pyridoxal-L-phosphate is in an aqueous solution at a concentration of about twenty (20) millimoles per liter of water.

3. The oral unit dose form of claim 1, wherein the methioninase enzyme is present in an amount of about 100 mg multiplied by weight of the individual in kilogram.

* * * * *